United States Patent [19]

Bachman et al.

[11] Patent Number: 4,697,450

[45] Date of Patent: Oct. 6, 1987

[54] GAS MONITOR HAVING TREND INDICATORS

[75] Inventors: Thomas E. Bachman, San Clemente; Larry S. McDavid, Anaheim; David M. Trueblood, Whittier, all of Calif.

[73] Assignee: Sensormedics Corporation, Anaheim, Calif.

[21] Appl. No.: 946,685

[22] Filed: Dec. 29, 1986

Related U.S. Application Data

[63] Continuation of Ser. No. 712,260, Mar. 15, 1985, abandoned.

[51] Int. Cl.⁴ .............................................. G01N 7/10
[52] U.S. Cl. ........................................ 73/23; 128/635; 204/406; 340/633
[58] Field of Search .................... 73/23; 204/406, 407, 204/403; 340/632, 633, 634; 128/635

[56] References Cited

U.S. PATENT DOCUMENTS

| | | | |
|---|---|---|---|
| 4,028,057 | 6/1977 | Nelson | 340/633 X |
| 4,207,146 | 6/1980 | Kunke | 204/406 |
| 4,340,885 | 7/1982 | Chavis et al. | 73/23 X |
| 4,355,533 | 10/1982 | Muldoon | 73/23.1 |
| 4,384,283 | 5/1983 | Drope et al. | 204/406 |
| 4,452,672 | 6/1984 | Parker et al. | 204/406 |

OTHER PUBLICATIONS

Article by Dr. A. M. Calverd, entitled, "Trend Indication for Digital Displays", from Design Ideas, Aug. 1982.

Primary Examiner—Stewart J. Levy
Assistant Examiner—Joseph W. Roskos
Attorney, Agent, or Firm—Lyon & Lyon

[57] ABSTRACT

An improved device for determining the trend of the partial pressure of a gas, such as oxygen or carbon dioxide, which diffuses outwardly through a patient's skin. The device, such as a cutaneous gas monitor, generates over time a series of partial pressure input values that are compared to one another for determining a trend in the partial pressure. This trend is communicated to the operator of the device.

3 Claims, 3 Drawing Figures

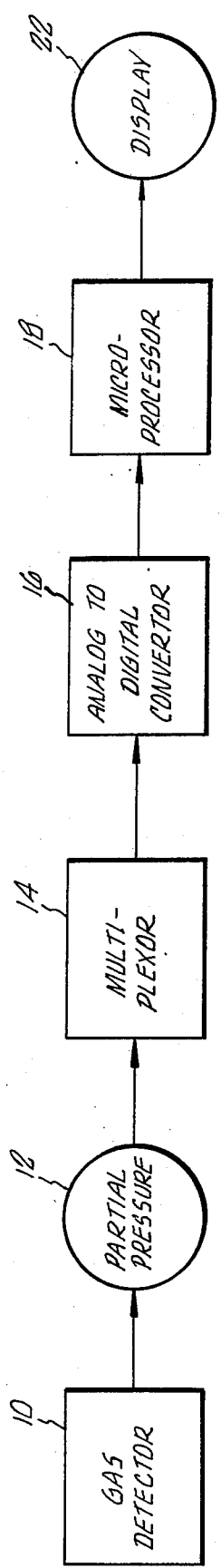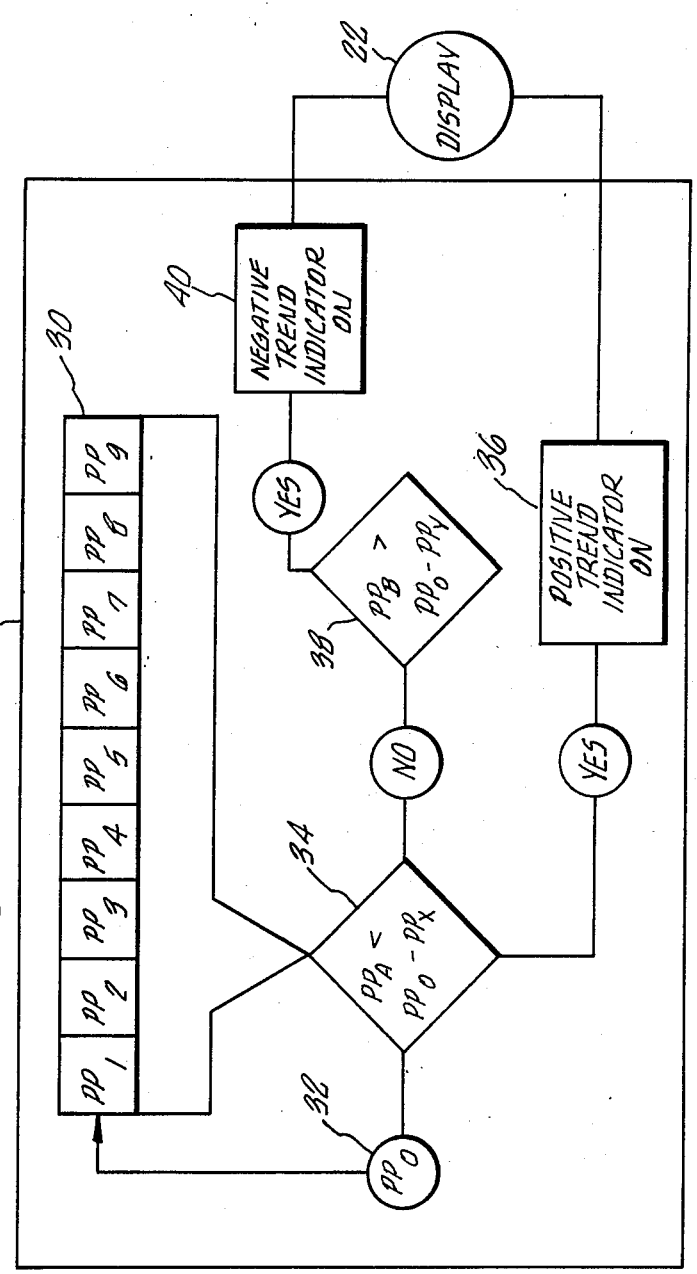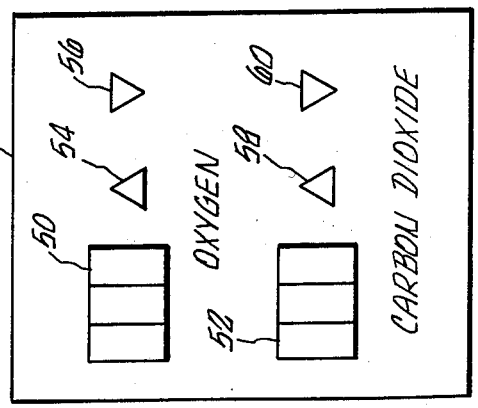

4,697,450

GAS MONITOR HAVING TREND INDICATORS

This a continuation of co-pending application Ser. No. 712,260 filed on Mar. 15, 1985 now abandoned.

BACKGROUND OF THE INVENTION

The present invention relates to cutaneous gas monitors and is directed more particularly to a feature used with the monitors that will alert an operator of the monitor to dangerous fluctuations in a body's metabolism.

Among the non-invasive patient monitoring instruments which have been developed recently is an instrument known as a cutaneous gas monitor. Gas monitors of this type make use of known gas detection techniques to measure the partial pressure of a gas, such as oxygen or carbon dioxide, which diffuses outwardly through a patient's skin. Cutaneous gas monitors have also been developed which simultaneously measure the partial pressure of both oxygen and carbon dioxide. One cutaneous gas monitor of the latter type is described in "Cutaneous Blood Flow and its Relationship to Transcutaneous $O_2/CO_2$ Measurements", by A. V. Beran, et al., "Critical Care Medicine", Vol. 9, No. 10, pp. 736–741 (1981).

Prior to this invention, cutaneous gas monitors displayed only the current partial pressures for oxygen and carbon dioxide. The current partial pressure was manually logged at various intervals so that the operator of the monitor could observe both the patient's current partial pressure and review the trend of these partial pressures over time. This method for determining the trend in the partial pressure is not totally desirable. The logging of readings is both time consuming and tedious, and the determination of a trend cannot be quickly or easily performed.

SUMMARY OF THE INVENTION

In accordance with the present invention there is provided an improved method and apparatus for determining the trend of partial pressures not subject to the above-described deficiencies.

Generally speaking, the apparatus of the present invention includes circuitry that receives input values relating to the current partial pressure of a constituent gas of a gas mixture being measured. The values are sequentially inputted to a multiplexor, analog to digital convertor and microprocessor to generate an output display. The display signals the current partial pressure.

Additionally, the display also includes trend indicators for signaling the trend of the partial pressure as a function of time. These trend indicators are controlled by the software programmed into the microprocessor. Generally, when an input value for a current partial pressure is communicated to the microprocessor the input value is transmitted to both a device for recording a stored partial pressure, and to a comparison device. Within the comparison device the current partial pressure is compared to a stored partial pressure. Should the difference in the current partial pressure and the stored partial pressure exceed a specified value a trend indicator is manifested on the display. The manifested trend indicator will correspond to the direction of the trend in the partial pressure; whether the trend is up or down. If the difference in the current and stored partial pressures does not exceed the specified value no trend indicator is manifested on the display.

DESCRIPTION OF THE DRAWINGS

Other objects and advantages of the present invention will be apparent from the following description and drawings in which:

FIG. 1 is a overall block diagram of the invention.

FIG. 2 is a pictorial of the display showing a current partial pressure signal and trend indicators.

FIG. 3 is a block diagram of the decision making process programmed in the microprocessor software.

DETAILED DESCRIPTION

Referring to FIG. 1, there is shown a gas detector or sensor 10 which samples a gas mixture. The gas detector determines the current partial pressure of one or more of the constituent gases in the gas mixture. One type of gas detector that can make this determination is an electrochemical cutaneous gas monitor.

The current partial pressure is an input 12 to a multiplexor 14. While the use of a multiplexor is not required, the multiplexor 14 can serve to select one output from various inputs. The output from the multiplexor 14 inputs to the analog to digital (A/D) convertor 16. The A/D convertor 16 serves to digitize the voltages at the output of the multiplexor 14 and apply them to the microprocessor 18 a multibit parallel form. An output is generated by the microprocessor 18 which is fed to the display 22.

Referring to FIG. 2, the display 22 is shown. The display 22 shows two lines of values; the first line for oxygen and the second line for carbon dioxide. Oxygen and carbon dioxide are the partial pressures most frequently measured by a cutaneous gas monitor. Within box 50 the current partial pressure for oxygen is signalled. Similarly, box 52 signals the current partial pressure for carbon dioxide. Trend indicator 54 is a positive trend indicator that is manifested if the increase in the oxygen partial pressure as a function of time is greater than a preset or adjustable amount, referred to herein as PPa. Trend arrow 56 is a negative trend indicator that is manifested if the decrease in the oxygen partial pressure as a function of the time is greater than a preset or adjustable amount, referred to herein as PPb. Similarly there is a positive trend indicator 58 and a negative trend indicator 60 shown for carbon dioxide. For clarity, the trend indicators can be triangularly shaped. The indicator pointing upward is manifested on the display when the current partial pressure is trending sufficiently upward. The indicator pointing downward is manifested on the display when the current partial pressure is trending sufficiently downwards. If the current partial pressure is not trending upward or downward sufficiently, neither trend indicator is manifested.

Referring to FIG. 3, the relevant portion of the logic sequence of the microprocessor is shown. The current partial pressure, PPo, inputs to the microprocessor 18. Within the microprocessor 18 PPo inputs to a device 30 for successively recording stored partial pressures. $PP_1$ through $PP_9$ represent nine stored partial pressures. While theoretically there is no limit to the number of stored partial pressures that can be recorded, a limited storage is generally necessary. Thus, after a period of time the oldest stored partial pressures will generally be erased. Neither is it generally necessary to continuously record the current partial pressure as a stored partial pressure. Thus, the stored partial pressures will generally be intermittently recorded. The interval of time between successive recordings of the partial pressure can be either preset or adjustable. Each successive stored partial pressure can be the current partial pressure, but it need not be. For example, the stored partial pressure can be the average of the current partial pressures for the time elapsed since the last stored partial pressure was recorded.

The current partial pressure also inputs to decision block 34 in the microprocessor 18. At decision block 34, PPa is compared to the difference between PPo and PPx. PPx represents any one of the stored partial pressures and is either preselected or adjustable. If PPa is less than the difference between PPo and PPx the positive trend indicator is manifested. If not, the logic sequence continues to decision block 38. At decision block 38, PPb is compared to the difference between PPo and PPy. PPy represents any one of the stored partial pressures and is either preselected or adjustable. If PPb exceeds the difference between PPo and PPy the negative trend indicator is manifested. The steps of this logic sequence are continually repeated over time. If more than one constituent gas is being monitored additional logic sequences are provided in the microprocessor 18.

A preferred embodiment is as follows. A cutaneous gas monitor is switched on. The operator selects a value for PPa and PPb. PPa and PPb generally have the same magnitude for ease of operation. Additionally, the operator selects an appropriate interval of time for PPx and PPy. A detector is applied to a patient and begins sampling the gas mixture diffusing outwardly through a patient's skin. The monitor determines the current partial pressure for a constituent gas. The current partial pressure is transmitted to a multiplexor which generates an output. The multiplexor output is applied to an A/D convertor. The output from the A/D convertor is feed to a microprocessor. The microprocessor is preset, by programming, to record a stored partial pressure every minute. The stored partial pressure is an average of the current partial pressures during the minute of time immediately preceding the time the stored partial pressure is recorded. The microprocessor is designed to store a maximum of forty-five stored partial pressures.

The logic sequence in the microprocessor compares PPa to the difference between PPo and PPx. Should PPa be less than the difference between PPo and PPx, a positive trend indicator is manifested on a display. If not, the logic sequence continues and compares PPb to the difference between PPo and PPy. Should PPb exceed the difference between PPo and PPy, a negative trend indicator is manifested on the display. The display also digitally signals the current partial pressure of the constituent gas.

Although the invention has been described in detail above, it is to be understood that this detailed description is by way of example only, and the protection granted is to be given a scope commensurate with the spirit of the invention and the following claims.

We claim as our invention:

1. A cutaneous gas monitor system comprising:
   means for sampling a gas mixture;
   means for determining a substanially current partial pressure of a constituent gas in the gas mixture;
   means for recording a series of stored partial pressures;
   means for adjustably selecting a historical value using the series of stored partial pressures;
   means for inputting at least one adjustably selected reference value to the monitor;
   means for comparing the current partial pressure, the historic value and the selected reference value to determine when the trend of the current partial pressure as a function of time exceeds the selected reference value;
   a display means for signalling the trend of the current partial pressure when the trend as a function of time exceeds the selected reference value.

2. The monitor system of claim 1 wherein the display means comprises a first and second indicator, the first indicator activating when the trend in the current partial pressure as a function of time exceeds, positively, a first adjustably selected reference value, and the second indicator activating when the trend in the current partial pressure as a function of time exceeds, negatively, a second adjustably selected reference value, 3. The monitor system of claim 1 wherein each sucessively stored partial pressure is a function of the current partial pressure for a selected interval of time proceeding the recording of the stored partial pressure.

* * * * *